United States Patent
Hirano et al.

(10) Patent No.: US 7,045,664 B2
(45) Date of Patent: May 16, 2006

(54) PROCESS FOR PRODUCING BISPHENOL A

(75) Inventors: Kazuyuki Hirano, Chiba (JP); Norio Ogata, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 10/525,528

(22) PCT Filed: Jul. 29, 2003

(86) PCT No.: PCT/JP03/09604

§ 371 (c)(1),
(2), (4) Date: Aug. 17, 2005

(87) PCT Pub. No.: WO2004/020377

PCT Pub. Date: Mar. 11, 2004

(65) Prior Publication Data

US 2006/0011541 A1  Jan. 19, 2006

(30) Foreign Application Priority Data

Aug. 28, 2002  (JP) .............................. 2002-248141

(51) Int. Cl.
C07C 37/82 (2006.01)
C07C 37/70 (2006.01)
C07C 37/68 (2006.01)

(52) U.S. Cl. ...................... 568/724; 568/716; 568/717; 568/723

(58) Field of Classification Search ................ 568/724, 568/723, 717, 716
See application file for complete search history.

(56) References Cited

U.S. PATENT DOCUMENTS 6,686,508 B1  2/2004  Hirano et al.

FOREIGN PATENT DOCUMENTS

| EP | 522700 | 1/1993 |
| JP | 5-331088 | 12/1993 |
| JP | 6-306002 | 11/1994 |
| JP | 11-090118 | 4/1999 |

*Primary Examiner*—Elvis O. Price
(74) *Attorney, Agent, or Firm*—Oblon, Spivak, McClelland, Maier & Neustadt, P.C.

(57) ABSTRACT

In a process for producing bisphenol A, an adduct of bisphenol A with phenol is promptly recovered in highly purity and high efficiency from a reaction mother liquor in the case of singling out bisphenol A from a reaction product. An adduct layer of bisphenol A with phenol is formed by crystallizing an adduct of bisphenol A with phenol from a solution of bisphenol A in phenol to form a slurry, the bisphenol A being produced by reacting phenol and acetone in the presence of an acid catalyst, subjecting the resultant slurry to a solid-liquid separation treatment, and thereafter removing the phenol from solid components, characterized by pouring onto a filter, a slurry solution of bisphenol A in phenol, the slurry solution containing in a crystalline state, an adduct of bisphenol A having an average particle size in the range of 0.05 to 1 mm with phenol, and filtering the slurry solution under reduced pressure in an atmosphere of an inert gas stream at 30 to 80° C. containing oxygen in a concentration of at most 5,000 ppm by volume.

4 Claims, No Drawings

PROCESS FOR PRODUCING BISPHENOL A

TECHNICAL FIELD

The present invention relates to a process for producing bisphenol A {2, 2-bis(4-hydroxyphenyl)propane}. More particularly, it pertains to a process for efficiently separating an adduct of bisphenol A with phenol in the above-mentioned process for producing bisphenol A.

BACKGROUND ART

It is well-known that bisphenol A is an important compound as a starting raw material for epoxy resin or an engineering plastic such as polycarbonate resin and polyarylene resin, and accordingly it tends to increasingly expand its demand year by year.

Bisphenol A is produced by the condensation reaction of excess phenol with acetone in the presence of an acidic catalyst and as the case may be, a sulfur compound etc. as a cocatalyst.

As a process for singling out bisphenol A from a reaction mixture, there are known a process comprising directly separating the same in the form of coarse crystal from the reaction mixture and a process comprising removing acetone, water and the like from the reaction mixture to leave a liquid mixture, thereafter concentrating cooling the resultant liquid mixture to precipitate an adduct of bisphenol A with phenol and separate the same into each other {(refer to Japanese Patent Application Laid-Open No. 91240/1976 (Show 51), Japanese Patent Application Laid-Open No. 77637/1982 (Show 57) and the like}.

The former process comprising directly separating bisphenol A in the form of coarse crystal from the reaction mixture suffers from such disadvantages as necessitating several times of cleaning owing to the microcrystalline property thereof, whereby product loss is increased.

Such being the case, there is prevalently carried out at the present time, the latter process comprising precipitating an adduct of bisphenol A with phenol and separating the same. In this case, the adduct of bisphenol A with phenol is crystallized, and the resultant crystal is separated form a mother liquor by a publicly well known solid-liquid separation method using filtration and/or a centrifugal separator {(refer to Japanese Patent Application Laid-Open No. 77637/1982 (Show 57), Japanese Patent Application Laid-Open No. 331088/1993 (Hei 5), Japanese Patent Application Laid-Open No. 275539/1988 (Show 63), Japanese Patent Application Laid-Open No. 107578/1994 (Hei 6), Japanese Patent Application Laid-Open No. 306002/1994 (Hei 6) and the like}.

In the above-mentioned solid-liquid separation method, there are usable a suction type belt filter and a drum filter in the separation by means of filtration method {(refer to Japanese Patent Application Laid-Open No. 306002/1994 (Hei 6)}. In this case, even if a high degree of vacuum is applied to suction for the purpose of removing the mother liquor on the surface of the crystals and decreasing intercrystalline liquid content in a short period of time, it is impossible to contrive marked decrease in the liquid content. Further on the other hand, there are brought about filter clogging and/or damage to a filter medium due to the adduct of bisphenol A with phenol depending upon the degree of opening of the selected filter or the material of the filter medium, thereby causing an obstacle to normal operation. On the contrary, an extremely low degree of vacuum, when applied to suction, requires a markedly long time in separating the mother liquor from the adduct of bisphenol A with phenol. In addition, impurities in the mother liquor are entrained into the next separation step and at the same time, are responsible for an increase in operational load and deterioration in the product quality. Moreover since the slurry of the reaction mixture and cleaning liquid are composed principally of phenol, unfavorable phenomena take place such that phenol is precipitated at a temperature lower than 30° C. and the adduct of bisphenol A with phenol adheres to a filter medium.

The method using a centrifugal separator {Japanese Patent Application Laid-Open NO. 107578/1994 (Hei 6), Japanese Patent Application Laid-Open NO. 306002/1994 (Hei 6)} is preferable with respect to decreasing intercrystalline liquid content and affording more dried product, but the substitution efficiency of the mother liquor, cleaning liquid or the like is made inferior to the substitution efficiency of the filtration method by the occurrence of crystal disintegration and the like due to centrifugal load imposed thereon. For these reasons, in order to improve the purity of the product in the case of treating a large amount of product, it is indispensable to generally repeat cleaning thereof by the use of a plurality of machines and instruments, whereby economically unfavorable results are brought about by increase in the number of machines and instruments and prolonged running hours.

DISCLOSURE OF THE INVENTION

The present invention has been made in the light of such circumstances as mentioned above, and the object thereof is to promptly recover the adduct of bisphenol A with phenol in high purity and high efficiency from the reaction mother liquor. In such circumstances, intensive extensive research and investigation were accumulated by the present inventors in order to achieve the above-mentioned objects. As a result, it has been found that an adduct of highly pure bisphenol A with phenol is obtainable in high efficiency by pouring a slurry solution of bisphenol A in phenol onto a filter, and forming an adduct layer of bisphenol A in crystalline state with phenol under specific conditions. The present invention has been accomplished on the basis of the foregoing findings and information.

That is to say, the present invention is summarized as follows.

1. A process for producing bisphenol A which comprises crystallizing an adduct of bisphenol A with phenol from a solution of bisphenol A in phenol to form a slurry, said bisphenol A being produced by reacting phenol and acetone in the presence of an acid catalyst, subjecting the resultant slurry to a solid-liquid separation treatment, and thereafter removing the phenol from solid components, characterized by pouring onto a filter, a slurry solution of bisphenol A in phenol, said slurry solution containing in a crystalline state, an adduct of bisphenol A with phenol having an average particle size in the range of 0.05 to 1 mm, and filtering said slurry solution under reduced pressure in an atmosphere of an inert gas stream at 30 to 80° C. containing oxygen in a concentration of at most 5,000 ppm by volume to constitute an adduct layer of bisphenol A with phenol.

2. The process for producing bisphenol A as set forth in the preceding item 1 wherein the reduced pressure is in the range of 30 to 95 kPa.

3. The process for producing bisphenol A as set forth in the preceding item 1 wherein the inert gas is nitrogen.

4. The process for producing bisphenol A as set forth in any of the preceding items 1 to 3 wherein the filter is a suction type endless belt filter.

THE MOST PREFERRED EMBODIMENT TO CARRY OUT THE INVENTION

In the process for producing bisphenol A according to the present invention bisphenol A is produced through (A) the step of reacting phenol and acetone; (B) the step of removing by produced water and low boiling point substances in the unreacted starting raw materials; (C) the step of concentrating the bisphenol A; (D) the step of crystallization/solid-liquid separation; (E) the step of dissolution/crystallization/solid-liquid separation for the adduct of bisphenol A with phenol at a ratio of 1:1 (hereinafter sometimes referred to as "phenol adduct"); (F) the step of heating/melting; (G) the step of removing phenol from bisphenol A; and (H) the step of granulation.

In what follows, some description will be given of each of the above-mentioned steps for producing bisphenol A.

(A) The Reaction Step

In the reaction step according to the present invention, bisphenol A is produced by subjecting excess phenol and acetone to condensation reaction in the presence of an acidic catalyst. An acid type ion exchange resin is usable as the above-mentioned acidic catalyst. The acid type ion exchange resin is not specifically limited, but may be selected for use from those that have hitherto been customarily employed as a catalyst for the production of bisphenol A. In particular, a sulfonic acid type cation exchange resin is suitable from the aspect of catalytic activity.

The aforesaid sulfonic acid type cation exchange resin is not specifically limited, provided that it is a strongly acidic cation exchange resin bearing a sulfonic acid group, but is exemplified by sulfonated styrene/divinyl benzene copolymer, sulfonated and crosslinked styrene polymer, phenol formaldehyde/sulfonic acid resin and benzene formaldehyde/sulfonic acid resin and the like. Any of the above-exemplified exchange resins may be used alone or in combination with at least one other.

In the reaction step, use is usually made of mercaptans as a cocatalyst in combination with the aforesaid acid type ion exchange resin. The mercaptans to be used therein, which are the compounds bearing at least one SH group in a free form in a molecule, can be selected for use from alkyl mercaptans and alkyl mercaptans which have at least one substituent such as carboxyl group, amino group and hydroxyl group and which are exemplified by mercaptocarboxylic acid, aminoalkanethiol and mercaptoalcohol. Specific examples of the mercaptans include alkyl mercaptans such as ethyl mercaptan, methyl mercaptan, n-butyl mercaptan and n-octyl mercaptan; thiocarboxylic acids such as thioglycol acid and β-mercapto-propionic acid; aminoalkane-thiols such as 2-aminoethanethiol and 2,2-dimethylthiazolidine; and mercaptoalcohols such as mercaptoethanol. Of these compounds, alkyl mercaptans are particularly preferable from the aspect of working effect as a cocatalyst. Any of the mercaptans may be used alone or in combination with at least one other. Further it is possible to immobilize any of the mercaptans onto the above-mentioned sulfonic acid type ion exchange resin, and cause the same to function as a cocatalyst. The amount of the mercaptan to be used is selected in the range of usually 0.1 to 20 mol %, preferably 1 to 10 mol % based on acetone as a starting raw material.

The ratio of phenol to acetone that are to be used in the process for producing bisphenol A according to the present invention is not specifically limited, but the amount of the unreacted acetone is preferably as small as possible in view of the easiness of refining the resultant bisphenol A, economical efficiency and the like factors. Accordingly, it is advantageous to use excess phenol over a stoichiometric amount thereof. Thus, phenol is used usually in an amount of 3 to 30 mol, preferably 5 to 15 mol per one mol of acetone. In the production of bisphenol A, a reaction solvent is unnecessary in general except for the case where the reaction liquid has unreasonably high viscosity or the reaction is conducted at such a low temperature that the operation is made difficult by solidification.

In the condensation reaction between phenol and acetone according to the present invention, which may be either a batch-wise system or continuous system, it is advantageous to use a continuous fixed-bed reaction system wherein phenol, acetone and mercaptan (in the case where the mercaptan is not immobilized on the sulfonic acid type ion exchange resin) are continuously supplied to a reactor which is filled in with the foregoing sulfonic acid type ion exchange resin to proceed with reaction. The reaction system may be constituted of either one reactor or a plurality of reactors that are arranged in series or parallel. For industrial use, it is particularly advantageous to adopt a continuous multi-stage fixed-bed reaction system composed of at least two reactors that are connected in series and each filled in with the sulfonic acid type ion exchange resin.

In the following, detailed description will be given of the reaction conditions of the continuous fixed-bed reaction system. In the first place, the acetone/phenol molar ratio is selected in the range of usually 1/30 to 1/3, preferably 1/15 to 1/5. The molar ratio, when being less than 1/30, brings about a fear of an unreasonably low rate of reaction, whereas the molar ratio, when being more than 1/3, results in a tendency to form an excessive amount of impurities, and lower the selectivity to bisphenol A. On the other hand, when the mercaptan is not immobilized on the sulfonic acid type ion exchange resin, the mercaptan/acetone molar ratio is selected in the range of usually 0.1/100 to 20/100, preferably 1/100 to 10/100. The molar ratio, when being less than 0.1/100, causes a fear of incapability of sufficiently exhibiting the working effect on enhancing the rate of reaction or the selectivity to bisphenol A, whereas the molar ratio, when being more than 20/100, results in that the effect on enhancing the same is not so recognized considering such a large amount.

Further the reaction temperature is selected in the range of usually 40 to 150° C., preferably 60 to 110° C. The reaction temperature, when being lower than 40° C., gives rise to an unreasonably low rate of reaction and besides, extremely high viscosity of the reaction liquid, thereby causing a fear of solidification as the case may be. On the contrary, the reaction temperature, when being higher than 150° C., leads to difficulty in reaction control, deterioration of selectivity to bisphenol A (p,p'-isomer) and further decomposition or deterioration of the cation exchange resin as the catalyst. The LHSV (liquid hourly space velocity) is selected in the range of usually 0.2 to 30 $hr^{-1}$, preferably 0.5 to 10 $hr^{-1}$.

(B) The Step of Removing Low Boiling Point Substances

In the step of removing low boiling point substances, the low boiling point substances are removed in a state that the reaction mixture which contains bisphenol A and which has been obtained in the above-mentioned (A) reaction step is substantially free from the acid type cation exchange resin, specifically a treatment for removing the low boiling point substances is put into practice by removing the catalyst by means of filtration or the like in the case of batch-wise reaction system, and as such without such a treatment in the case of continuous fixed-bed reaction system.

In the above-mentioned step, the low boiling point substances such as unreacted acetone, by-produced water and alkyl mercaptan are firstly removed by vacuum distillation using a distillation tower.

The vacuum distillation is put into practice usually under the conditions including a pressure of 6.5 to 80 kPa and a temperature of 70 to 180° C. In this case, unreacted phenol is azeotropically distilled, and a part thereof is distilled away together with the above-mentioned low boiling point substances through the top of the distillation tower to the outside of the removing system. It is preferable in this distillation to set the temperature of a heating source to be used on 190° C. or lower for the purpose of preventing the thermal decomposition of bisphenol A. As the material of construction for the machinery and equipment, there are generally used stainless steel type SUS304, SUS316 and SUS316L.

(C) The Concentration Step

Since bisphenol A, phenol and the like are contained in the bottom wherein the low boiling point substances have been removed from the reaction mixture, the phenol is distilled away by means of vacuum distillation to concentrate the bisphenol A. The conditions of the concentration are not specifically limited, but the concentration is usually carried out under the conditions including a temperature in the range of 100 to 170° C., approximately and a pressure in the range of 5 to 70 kPa. The concentration temperature, when being lower than 100° C., unfavorably requires a high degree of vacuum, whereas the concentration temperature, when being higher than 170° C., unfavorably necessitates excess heat removal in the subsequent crystallization step. The concentration of bisphenol A in the concentrated residual liquid is in the range of preferably 20 to 50% by mass, more preferably 20 to 40% by mass. The concentration thereof, when being lower than 20% by mass, brings about lowered recovery rate of bisphenol A, whereas the concentration thereof, when being higher than 50% by mass, gives rise to a fear that the slurry transfer after crystallization is made difficult (D) The Step of Crystallization/Solid-Liquid Separation The present invention is characterized by the conditions and prerequisites for solid-liquid separation step in the step of crystallization/solid-liquid separation. The step of crystallization/solid-liquid separation is the step of crystallizing and separating the phenol adduct from the concentrated residual liquid which has been obtained in the preceding concentration step (C)

In this step, the above-mentioned concentrated residual liquid is firstly cooled to 40 to 70° C., approximately to crystallize the phenol adduct into slurry. In this case, the cooling may be conducted by the use of an external heat exchanger or by a vacuum cooling crystallization method which comprises adding water to the concentrated residual liquid, and cooling the liquid under reduced pressure taking advantage of the latent heat of water vaporization. In the aforesaid method, crystallization treatment is performed usually under the conditions including a temperature in the range of 40 to 70° C. and a pressure in the range of 4 to 16 kPa by adding water in an amount of 3 to 20% by mass approximately to the concentrated residual liquid. The water to be added, when being less than 3% by mass, causes insufficient heat-removal capacity, whereas the water, when being more than 20% by mass, unfavorably leads to an increase in dissolution loss of bisphenol A. Moreover, a crystallization temperature, when being lower than 40° C., gives rise to a fear of an increase in the viscosity of crystallization liquid or solidification of the same, whereas the temperature, when being higher than 70° C., unfavorably brings about an increase in dissolution loss of bisphenol A.

The slurry containing the crystallized phenol adduct contains the phenol adduct in a crystalline state having an average particle size in the range of 0.05 to 1 mm, preferably 0.1 to 0.9 mm. In the present invention, the slurry is separated into the phenol adduct and crystallization mother liquor containing reaction byproduct by means of filtration method. The above-mentioned average particle size, when being smaller than 0.05 mm, leads to deterioration in the cleaning effect due to enlarged surface area of the particles, whereas the average particle size, when being larger than 1 mm, gives rise to unreasonably high settling velocity of the particles, which are more liable to unfavorably stagnate in the lower portion of transport piping. The filtration method can enhance the substitution efficiency of a solvent on cleaning therewith as compared with the centrifugal separation method, thereby enabling effective removal of impurities that are contained on the surfaces of and among the crystals. The crystallization mother liquor which contains microcrystals passing through a filter medium may be recycled through the reactor in part as such, and subjected at least in part to alkali decomposition treatment so as to recover the same as phenol and isopropenylphenol. Alternatively, the above-mentioned mother liquor may be isomerized in part or in whole and recycled to the raw material for crystallization {refer to Japanese Patent Application Laid-Open NO. 321834/1994 (Hei 6)}.

The filtration method as mentioned hereinabefore is adopted in a first crystallization/solid-liquid separation according to the present invention usually by the use of a dry filter, tray filter or suction type belt filter which are conventionally used. Of these, a suction type endless belt filter is particularly preferable.

By filtering the slurry solution of bisphenol A of phenol (1) in which the adduct of bisphenol A with phenol is contained in a crystalline state as mentioned above by using a filter, an adduct layer of bisphenol A in a crystalline state with phenol is formed on the aforesaid filter, and thereafter the adduct layer is cleaned with a cleaning liquid. There are usable as a cleaning liquid, the recovered phenol which has been obtained in the above-mentioned concentration step (C) or the cleaning water after being used in the next step of dissolution/crystallization/solid-liquid separation (E).

It is necessary to promptly carry out the above-described procedures of filtration and cleaning under reduced pressure in order to enhance the substitution efficiency of a solvent. The degree of evacuation, when being unreasonably low, gives rise to a failure of separation into the phenol adduct and the mother liquor, or causes an excessively long time for separation, whereas the degree of evacuation, when being unreasonably high, results in too much load imposed on the filter, thus leading to cause for filter failure. The degree of evacuation is preferably 30 to 95 kPa, more preferably 40 to 90 kPa.

It is also necessary to set the temperature of an atmosphere containing the filter on 30 to 80° C., preferably 35 to 50° C. Unless the atmosphere is kept at a suitable heated state, there are caused solidification of the mother liquor and cleaning liquid and conversely, dissolution of once crystallized phenol adduct, since the mother liquor and cleaning liquid are composed principally of phenol.

Moreover since the filtration procedure is accompanied with gas/liquid mixing, it is preferable to remove as much as possible from the atmosphere, such substances as oxygen which affect bisphenol A or phenol in the subsequent step. It is important to perform the removal step in a stream of an inert gas containing oxygen of at most 5,000 ppm by volume, preferably at most 3,000 ppm by volume. The inert gas to be used is not specifically limited, but is preferably nitrogen from the economical point of view.

For the purpose of obtaining the objective product of high purity, it is effective to repeat the step of crystallization/solid-liquid separation a plurality of times. That is to say in the present invention, the step of crystallization/solid-liquid separation (D) and the next step of dissolution/crystallization/solid-liquid separation for the adduct of bisphenol A with phenol (E) are repeated a plurality of times, and thereafter the step of heating/melting (F) proceeds, followed by the step of removing phenol (G).

(E) The Step of Dissolution/Crystallization/Solid-Liquid Separation for the Adduct of Bisphenol A with Phenol The phenol adduct which has been crystallized and separated in the step (D) is dissolved with a phenol-containing solution. The phenol-containing solution to be used in the present step is not specifically limited, but can be exemplified by the recovered phenol which is obtained in the above-described concentration step (C), the cleaning liquid which is used for the phenol adduct and is formed in the step of crystallization/solid-liquid separation (D) and the mother liquor in the solid-liquid separation of crystallized phenol adduct and the cleaning liquid for the phenol adduct, said liquor and liquid being formed in the present step (E) and/or subsequent steps.

In the present step, the above-mentioned phenol-containing solution is added to the phenol adduct obtained in the step (D), and the resultant mixture is heated to 80 to 110° C., approximately to dissolve the phenol adduct by heating and to prepare a bisphenol A-containing solution which has a bisphenol A concentration favorable for the crystallization procedure. By dissolving the adduct layer after cleaning in phenol, followed by crystallization in the above-mentioned manner, there is obtained a slurry solution of bisphenol A in phenol (2) which solution contains the adduct of bisphenol A with phenol in a crystalline state.

The slurry solution of bisphenol A in phenol (2) which is prepared in the aforesaid manner has a low viscosity even at a relatively low temperature, is comparatively easy to handle, and is well suited for filtration with a filter. The step of dissolution/crystallization/solid-liquid separation of the phenol adduct is repeated a plurality of times.

(F) The Step of Heating/Melting . . .

The step of heating/melting is a step of heating/melting the phenol adduct which has been crystallized and separated in the above-described step (E). In this step, the phenol adduct is heated to 100 to 160° C., approximately and is molten into a liquid mixture.

(G) The Step of Removing Phenol . . .

The step of removing phenol is a step of distilling away the phenol by means of vacuum distillation to recover bisphenol A in a molten state. The above-mentioned vacuum distillation is put into practice under the conditions generally including a pressure in the range of 1.3 to 13.3 kPa and a temperature in the range of 150 to 190° C. The residual unremoved phenol can further be removed by steam stripping (H) The Step of Granulation . . .

The step of granulation is a step of making into droplets, the bisphenol A in a molten state which has been obtained in the preceding step (G) by the use of a granulation apparatus such as a spray dryer so that the bisphenol A is cooled/solidified into the objective product. In this case, the droplets are formed by atomization, spraying or the like, and are cooled with nitrogen, air or the like.

EXAMPLES

In what follows, the present invention will be described in more detail with reference to comparative examples and working examples, which however shall never limit the present invention thereto.

Preparation Example 1

A reactor which had been filled in with 600 g of a cation exchange resin was continuously charged with 4, 600 g/hr feed rate of phenol, 280 g/hr feed rate of acetone and 16 g/hr feed rate of ethyl mercaptan, while the temperature was maintained at 75° C. The resultant reaction mixture was sent to a step of removing low boiling point substances intended for removing low boiling point substances composed principally of unreacted acetone with a result that the low boiling point substances composed principally of unreacted acetone were removed. As a result, there was obtained a reaction product at a rate of 4, 640 g/hr which was composed principally of bisphenol A and unreacted phenol that were formed in the step of removing low boiling point substances. The reaction product, from which part of phenol was removed under the conditions including a temperature of 165° C. and a pressure of 53.3 kPa, was concentratedly regulated so that the concentration of the bisphenol A was made to be 30% by mass. To the resultant bisphenol A concentrate was added 5% by mass of water, and the resultant mixture was subjected to cooling/crystallization under stirring at 45° C. to crystallize a phenol adduct, which had an average particle size in a crystalline state of 0.1 mm.

Example 1

The slurry solution at 45° C. of bisphenol A and phenol in an amount of 3,000 g which had been obtained in the Preparation Example 1 was poured onto a filter on which a stainless steel wire mesh of 63 micrometer (μm) was laid down, and the temperature of which was raised to 46° C., approximately in an atmosphere of nitrogen at 50° C. containing 1,200 ppm by volume of oxygen, and was filtered by suction at 80 kPa for 60 seconds. As a result, the above-mentioned slurry solution was separated into the phenol adduct and mother liquor with a result that a wet cake having a thickness of 84 mm, approximately and a liquid content of 25% by mass was obtained on the stainless steel wire mesh. The resultant wet cake was dried in a stream of nitrogen at room temperature and reduced pressure for 24 hours. Subsequently a measurement was made of the average particle size of the resultant adduct. The result was 0.3 mm. In addition, a measurement was made of Hazen color index of molten adduct. The result was APHA 5.

Comparative Example 1

The procedure in Example 1 was repeated except that the slurry solution was poured onto the filter under atmospheric pressure instead of sucking at 80 kPa. The slurry solution was allowed to stand for 10 minutes, but it was impossible to separate by filtration into a precipitate and supernatant layer, and recover as a cake.

Comparative Example 2

The procedure in Example 1 was repeated except that the slurry solution was poured onto a filter at room temperature (about 20° C.) instead of the filter the temperature of which was raised to 46° C., approximately. As a result, there was observed a phenol deposit on the circumference of the filter. The resultant wet cake was analyzed by means of thin layer chromatography. As a result, the ratio of bisphenol A/phenol was 1/2.3, pointing out that the cake was a mixed cake containing crystalline phenol adduct and free phenol in part.

Comparative Example 3

The procedure in Example 1 was repeated except that the slurry solution was poured onto a filter the temperature of which was raised to 105° C., approximately in an atmosphere of nitrogen at 95° C. instead of the filter the temperature of which was raised to 46° C., approximately in an atmosphere of nitrogen at 50° C. As a result, phenol adduct was hardly left on the top portion of the filter, whereby no wet cake was obtained.

Comparative Example 4

The procedure in Example 1 was repeated except that the slurry solution was filtered in an atmosphere of air instead of an atmosphere of nitrogen at 50° C. containing 1,200 ppm by volume of oxygen, a phenol adduct sample (APHA of 5.5) which had been treated in the same manner as in Example 1 was molten in an atmosphere of nitrogen at 165° C., and the phenol was distilled away under reduced pressure to obtain bisphenol A. The Hazen color index of the molten adduct was APHA 18.

Example 2

The phenol adduct sample which had been obtained in Example 1 was molten in an atmosphere of nitrogen at 165° C., and the phenol was distilled away under reduced pressure to obtain bisphenol A. The Hazen color index of molten adduct was APHA 10. It can be seen from the result that filtration treatment in an atmosphere of nitrogen brings about less coloring and a more favorable result as compared with that in an atmosphere of air.

Industrial Applicability

According to the process for producing bisphenol A of the present invention it is made possible to promptly recover a highly pure adduct of bisphenol A with phenol in high efficiency from a reaction mother liquor by pouring the slurry solution of bisphenol A and phenol onto a filter, and forming an adduct layer of bisphenol A with phenol in a crystalline state under specific conditions. In addition thereto, by specifically defining the average particle size of the phenol adduct to 0.05 to 1 mm in the step of crystallization and solid-liquid separation which step constitutes the essential element in the present invention, it is made possible to enhance the filtration efficiency and cleaning efficiency, and at the same time to obtain bisphenol A with less coloring.

The invention claimed is:

1. A process for producing bisphenol A which comprises crystallizing an adduct of bisphenol A with phenol from a solution of bisphenol A in phenol to form a slurry, said bisphenol A being produced by reacting phenol and acetone in the presence of an acid catalyst, subjecting the resultant slurry to a solid-liquid separation treatment, and thereafter removing the phenol from solid components, characterized by pouring onto a filter, a slurry solution of bisphenol A in phenol, said slurry solution containing in a crystalline state, an adduct of bisphenol A with phenol having an average particle size in the range of 0.05 to 1 mm, and filtering said slurry solution under reduced pressure in an atmosphere of an inert gas stream at 30 to 80° C. containing oxygen in a concentration of at most 5,000 ppm by volume to constitute an adduct layer of bisphenol A with phenol.

2. The process for producing bisphenol A according to claim 1 wherein the reduced pressure is in the range of 30 to 95 kPa.

3. The process for producing bisphenol A according to claim 1 wherein the inert gas is nitrogen.

4. The process for producing bisphenol A according to claim 1 wherein the filter is a suction type endless belt filter.

* * * * *